(12) United States Patent
Müller et al.

(10) Patent No.: US 10,278,755 B2
(45) Date of Patent: *May 7, 2019

(54) DOUBLE THREADED GUIDANCE OR STIFFENING WIRE FOR MULTIPLE USE VERTEBRAL AUGMENTATION (VA) BALLOON

(71) Applicant: DePuy Synthes Products, Inc., Raynham, MA (US)

(72) Inventors: Marc Müller, Weil am Rhein (DE); Kris Chavatte, Küsnacht (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/824,516

(22) Filed: Nov. 28, 2017

(65) Prior Publication Data

US 2018/0168705 A1 Jun. 21, 2018

Related U.S. Application Data

(63) Continuation of application No. 14/797,720, filed on Jul. 13, 2015, now Pat. No. 9,855,086, which is a
(Continued)

(51) Int. Cl.
*A61B 17/88* (2006.01)
*A61M 25/10* (2013.01)
(Continued)

(52) U.S. Cl.
CPC ...... *A61B 17/8855* (2013.01); *A61B 17/8802* (2013.01); *A61B 17/8897* (2013.01);
(Continued)

(58) Field of Classification Search
CPC ............. A61M 25/10; A61M 25/0102; A61M 25/0169; A61M 25/09041; A61M 25/0905
See application file for complete search history.

(56) References Cited

U.S. PATENT DOCUMENTS 4,606,347 A 8/1986 Fogarty et al.
4,846,174 A 7/1989 Willard et al.
(Continued)

FOREIGN PATENT DOCUMENTS

WO 2007/075788 7/2007

OTHER PUBLICATIONS

CareFusion Corporation, "AVAmax Advanced Vertebral Augmentation System," (product sheet), carefusion.com, 2010, 20 pages.
(Continued)

*Primary Examiner* — Anu Ramana
(74) *Attorney, Agent, or Firm* — Meunier Carlin & Curfman LLC

(57) ABSTRACT

A catheter device that includes a double-threaded guidance wire that allows multiple use of a compliant cavity creation device (i.e., treatment of more than one level). The double-threaded guidance wire may be connected with the luer part of the device and a distal part of the balloon using a threaded engagement to avoid lengthening of the inner tube, avoid lengthening of the balloon, and to limit the plastic deformation of the system in axial direction. In other implementations, the double-threaded guidance wire may be reconnected to the distal part of the balloon with a distal thread of the double-threaded guidance wire in order to restore the nominal length.

21 Claims, 7 Drawing Sheets

Related U.S. Application Data continuation of application No. 12/904,975, filed on Oct. 14, 2010, now Pat. No. 9,101,430.

(51) Int. Cl.
*A61M 31/00* (2006.01)
*A61M 25/00* (2006.01)
*A61B 17/00* (2006.01)

(52) U.S. Cl.
CPC .... *A61M 25/0026* (2013.01); *A61M 25/0097* (2013.01); *A61M 25/1025* (2013.01); *A61M 31/005* (2013.01); *A61B 2017/00557* (2013.01); *A61M 2025/1079* (2013.01)

(56) References Cited

U.S. PATENT DOCUMENTS

| | | | |
|---|---|---|---|
| 5,035,686 | A | 7/1991 | Crittenden et al. |
| 5,271,415 | A | 12/1993 | Foerster et al. |
| 5,409,470 | A | 4/1995 | McIntyre et al. |
| 6,719,773 | B1 | 4/2004 | Boucher et al. |
| 6,860,901 | B1 | 3/2005 | Baker et al. |
| 2004/0102774 | A1 | 5/2004 | Trieu |
| 2007/0173939 | A1 | 7/2007 | Kim et al. |
| 2007/0270876 | A1 | 11/2007 | Kuo et al. |
| 2008/0183204 | A1 | 7/2008 | Greenhalgh et al. |
| 2008/0195207 | A1 | 8/2008 | Lin et al. |
| 2008/0288078 | A1 | 11/2008 | Kohm et al. |
| 2008/0294205 | A1 | 11/2008 | Greenhalgh et al. |
| 2009/0177236 | A1 | 7/2009 | Saab et al. |
| 2009/0292323 | A1 | 11/2009 | Chirico et al. |
| 2009/0306597 | A1 | 12/2009 | Lupton et al. |

OTHER PUBLICATIONS

Kyphon, Inc., "Advances in Minimally Invasive Spine Therapies: The Mechanics of Balloons Moving Bone," 2004, 8 pages.

Kyphon, Inc., KYPHON®, KyphX Express™ System, Reducing the Profile. Increasing Your Options, 2004, 2005, 4 pages.

Kyphon, Inc., "KyphX Xpander Inflatable Bone Tamp," (product sheet), www.kyphon.com, 2005, 4 pages.

Kyphon, Inc., "Verfahrenstechnik Balloon-Kyphoplastie," (product sheet), www.kyphon-eu.com, pp. 1-12.

Kyphon, Inc., "Verfahrenstechnik Balloon-Kyphoplastie," (product sheet), www.kyphon-eu.com, pp. 13-15.

Magerl, F., et al., "A Comprehensive Classification of Thoracic and Lumbar Injuries," European Spine Journal, vol. 3, Springer-Verlag, 1994, pp. 184-201.

Stryker Instruments, "iVAS Inflatable Vertebral Augmentation System," (product sheet), www.stryker.com, 2010, 2 pages.

Synthes, "VBS-Vertebral Body Stenting System," Minimally invasive percutaneous, reconstructive treatment for vertebral body fractures (technique guide), Feb. 2009, 40 pages.

International Preliminary Report on Patentability and Written Opinion, dated Apr. 16, 2013, received in connection with International Application No. PCT/US2010/052717.

International Search Report and Written Opinion, dated Nov. 21, 2011, received in connection with International Application No. PCT/US2010/052717.

DOUBLE THREADED GUIDANCE OR STIFFENING WIRE FOR MULTIPLE USE VERTEBRAL AUGMENTATION (VA) BALLOON

CROSS-REFERENCE TO RELATED APPLICATIONS

This application is a continuation of U.S. patent application Ser. No. 14/797,720 filed Jul. 13, 2015, which is a continuation of U.S. patent application Ser. No. 12/904,975 filed on Oct. 14, 2010 (now U.S. Pat. No. 9,101,430) entitled "DOUBLE THREADED GUIDANCE OR STIFFENING WIRE FOR MULTIPLE USE VERTEBRAL AUGMENTATION (VA) BALLOON," which are incorporated herein by reference in their entirety.

BACKGROUND

Osteoporosis is a disease that gradually weakens bones and causes them to become brittle. Left untreated, osteoporosis can progress painlessly until a bone breaks. In some cases, osteoporosis can cause compression fractures in the spine. This occurs when the bony block, or vertebral body, in the spine collapses. This causes severe pain, deformity, and loss of height. It can also lead to nerve compression.

Until recently, doctors were limited in how they could treat osteoporosis-related spine fractures. For example, typical options included pain medications, bed rest, bracing or invasive spinal surgery. More recently, the vertebroplasty and kyphoplasty procedures have become available as therapeutic and preventive treatments for compression fractures. Vertebroplasty involves passing a bone needle slowly through the soft tissues of the back to deposit a small amount of orthopedic cement, called polymethylmethacrylate (PMMA) into the vertebral body. PMMA is a medical grade bone cement that has been used for many years in a variety of orthopaedic procedures.

Kyphoplasty is a procedure that involves making small incisions and placing a catheter into the vertebral space where the fracture is located. A cavity is created inside the bone (e.g. drilled) and a balloon, called a bone tamp, is inserted. The balloon may be support by a guidance wire that is passed through a central lumen of the catheter. The balloon is then inflated with contrast medium until it expands to a desired height, deflated and removed. The balloon is used to expand and reposition the compressed bone, and to create a cavity for cement. The cavity created by the balloon may then be filled with PMMA, binding the fracture. Kyphoplasty substantially restores height to the spine, thus reducing deformity (also pain relief).

However, the majority of the balloons utilized by kyphoplasty catheters are made of a ductile (compliant) material. Ductile materials initially undergo elastic (reversible) deformation, followed by plastic (permanent) deformation after reaching a yield point. Therefore, when the balloon is inflated in bone to reduce a fracture, it undergoes some permanent deformation (e.g., deformation of the inner tube and deformation of the balloon). As such, reinflation of the balloon will be biased. Reinserting the guidance wire would result in a non-supported distal balloon part because of the lengthening of the balloon that results from plastic deformation. Therefore, the balloon should not be reused.

SUMMARY

Described herein is a tool that enables multiple use (i.e., reuse) of a catheter for example in a multi-level vertebral augmentation procedure. As described below, the tool may include a balloon catheter that may be a two (or more) lumen catheter. An outer lumen may be used for inflation of the balloon and an inside lumen for guiding a double-threaded guidance wire. A thread in the distal part of the guidance wire may be provided with outer diameter of the distal thread being less than the inner diameter of an inner tube of the catheter. The construction of the thread (i.e., outer diameter, inner diameter, flank lead, length) can be standard design (ISO, Metric) or any design allowing a locking mechanism. The counter piece (e.g., a distal threaded nut) for the distal thread of the guidance wire may be disposed inside the balloon of the catheter and connected to the inner tube. This nut can also be used as a radiopaque marker inside the balloon.

The guidance wire may also have a proximal thread with an outer diameter greater than an outer diameter distal thread. The construction of the thread (e.g., outer diameter, inner diameter, flank lead, length) can be standard design (ISO, Metric) or any design allowing a locking mechanism. The counter piece (e.g., a proximal threaded nut) for the proximal thread of the guidance wire may be disposed inside a luer connector (e.g., a connector for balloon inflation) of the catheter and positioned coaxial to the inner tube. The length of the proximal threaded nut may be longer than the distal threaded nut to account for changes of the balloon catheter during inflation.

In one implementation, the double-threaded guidance wire may remain connected to the balloon during inflation to prevent the balloon and the inner tube from lengthening, substantially avoiding plastic deformation in an axial direction. In another implementation, the double-threaded guidance wire may be removed from the tool during balloon inflation. Thereafter, the double-threaded guidance wire can be reinserted into the tool to connect to the thread in the balloon to restore the pre-inflation nominal balloon axial length and stiffness before inflation. Thus, after first use of the tool, it can be reinserted and used again, as the same catheter length and balloon length is preserved with only minor plastic deformation in axial direction.

In some implementations, there is provided a reusable tool that includes a handle having a proximal thread. A catheter structure may be included that has an outer body and an inner body. The outer body may be connected to a fitting of the handle. An expandable structure may be connected to the outer body, where the expandable structure has a distal thread affixed within an interior thereof. A guidance wire maybe disposed within the inner body, where the guidance wire has a first threaded portion adapted to engage the proximal thread and a second threaded portion adapted to engage the distal thread.

In other implementations, there is provided a reusable tool for treating a vertebral body. The tool may include a handle having an inflation port and a proximal thread. A dual-lumen catheter may be connected to a fitting of the handle and a balloon connected to the outer body. The balloon may have a distal thread affixed within an interior thereof. A guidance wire may be disposed within an inner lumen of the dual-lumen catheter, where the guidance wire has a first threaded portion adapted to engage the proximal thread in the handle and a second threaded portion adapted to engage the distal thread in the balloon.

In yet other implementations, there is provided a tool for treating a vertebral body that includes a handle having an inflation port, a luer fitting and a proximal thread disposed with a body of the handle. A catheter body may be attached to the luer fitting of the handle. A balloon may be connected to the catheter body, where the balloon has a distal thread affixed within an interior thereof. The tool may further include a dual-threaded guidance wire having a first threaded portion adapted to engage the proximal thread and a second threaded portion adapted to engage the distal thread.

In accordance with further implementations there is provided a method for treating bone with a tool having a catheter tube assembly. The method may include fixing a double-threaded guidance wire to a distal threaded nut of an inflatable structure, and deploying the inflatable structure inside a first location of the bone. The inflatable structure may be inflated to create a cavity within a treatment area of the bone, after which the inflatable structure is deflated and removed from inside the bone. The inflatable structure may then be reused and reinserted within the treatment area or inside a second location of the bone.

This summary is provided to introduce a selection of concepts in a simplified form that are further described below in the detailed description. This summary is not intended to identify key features or essential features of the claimed subject matter, nor is it intended that this summary be used to limit the scope of the claimed subject matter. Furthermore, the claimed subject matter is not limited to implementations that solve any or all disadvantages noted in any part of this disclosure.

BRIEF DESCRIPTION OF THE DRAWINGS

To facilitate an understanding of and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein.

DETAILED DESCRIPTION

Referring now to FIGS. 1-6, there is illustrated aspects of a reusable tool 100 that includes a double-threaded guidance or stiffening wire 112. The tool 100 includes a catheter tube assembly 104 made from, e.g., metal or extruded plastic materials. In some implementations, the catheter tube may be generally flexible. The distal end of the catheter tube assembly 104 carries a balloon structure 106, which is made, e.g., from a deformable plastic or other compliant material. In use, the balloon structure 106 is deployed and expanded inside bone, e.g., in a vertebral body, to compact cancellous bone and/or displace cortical bone.

Figure 1:
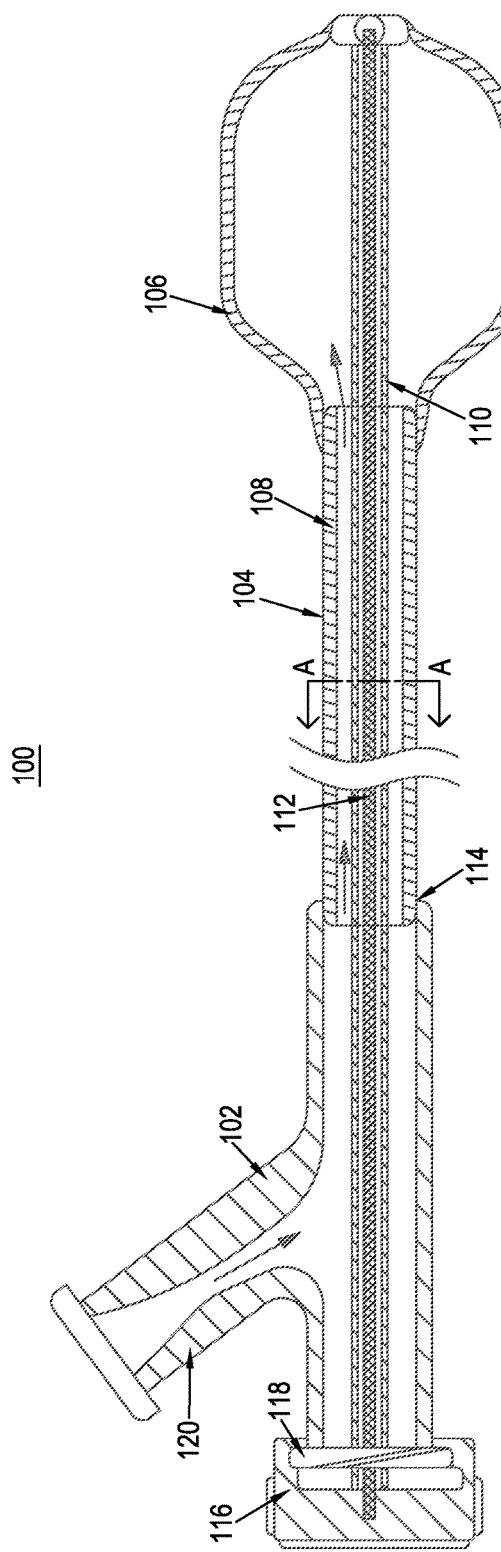
FIG. 1 is a view of a reusable tool having an balloon structure.
Figure 2:
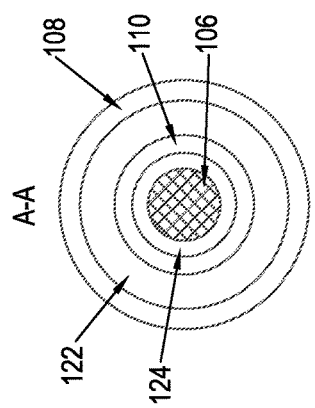
FIG. 2 is a cross-sectional view of a catheter tube assembly of the reusable tool of FIG. 1.

As best shown in FIGS. 1 and 2, the catheter tube assembly 104 includes an outer catheter body 108 and an inner catheter body 110. The inner catheter body 110 extends through and beyond the outer catheter body 108 into the balloon structure 106. The proximal ends of the inner catheter body 110 and the outer catheter body 108 are jointly coupled to the distal end of a luer fitting 114 on a y-shaped luer connector 102, which serves as a handle for the tool 100.

As shown in FIG. 1, the proximal end of the inner catheter body 110 extends within the luer connector 102 beyond the coupled proximal ends of the outer catheter body 108. The extended proximal end of the inner catheter body 110 is coupled to the luer connector 102 at a location proximal to an inflation port 120. The distal end of the inner catheter body 110 extends beyond the distal end of the outer catheter body 108.

The balloon structure 106 is coupled at its proximal end to the distal end of the outer catheter body 108. The balloon structure 106 is coupled at its distal end to the double-threaded guidance wire 112 that extends beyond the distal end of the inner catheter body 110. The double-threaded guidance wire 112 is coupled at its proximal end to a rotatable luer cap 116.

As shown in FIG. 2, the interior diameter of the outer catheter body 108 is larger than the exterior diameter of the inner catheter body 110. An interior passage 122 is thereby defined between them. In use, the interior passage 122 conveys a pressurized flowable medium, e.g., sterile water, radiopaque fluid, gas, or other flowable substance into the balloon structure 106, to expand it. The inflation port 120 on the luer connector 102 (see, e.g., FIG. 1) serves, in use, to couple the interior passage 122 to the source of pressurized flowable medium (not shown). The inner catheter body 110 defines an interior lumen 124 within the interior passage 122. The double-threaded guidance wire 112 extends through the interior lumen 124.

Figure 3:
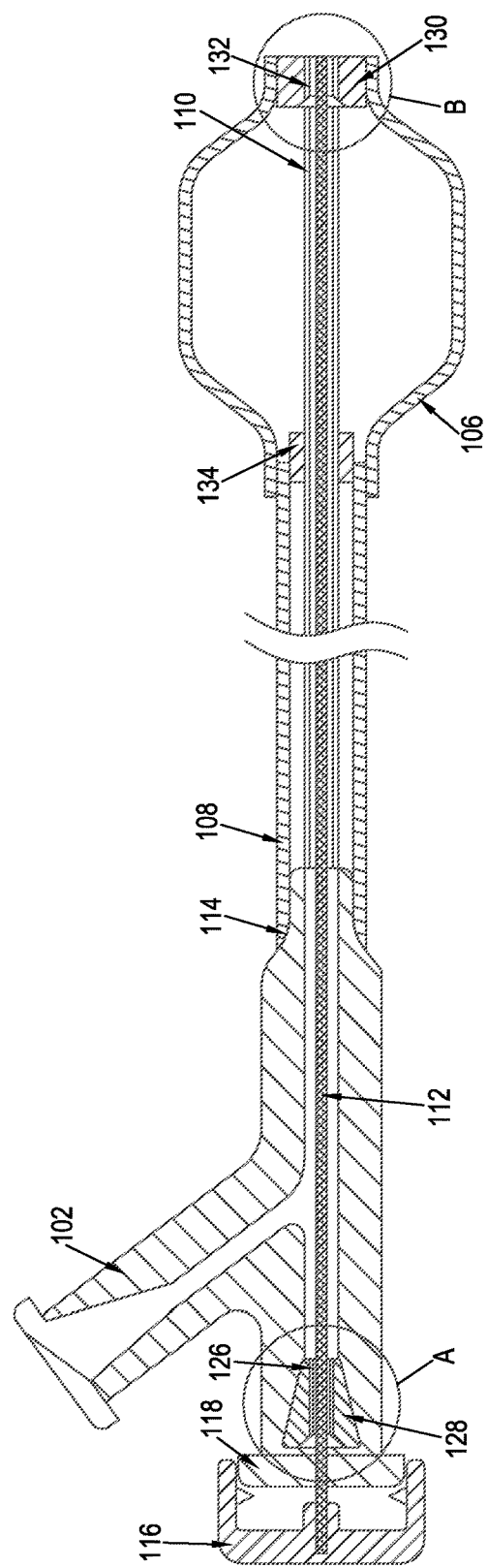
FIG. 3 is a view of the reusable tool of FIG. 1 showing additional details of a double-threaded guidance wire.

With reference to FIGS. 1 and 3, the luer cap 116 rotates about a proximal luer fitting 118 on the luer connector 102. Twisting the luer cap 116 rotates the double-threaded guidance wire 112 within the inner catheter body 110. The torque caused by twisting the luer cap 116 is transmitted to a first threaded portion 126 of the double-threaded guidance wire 112 that engages a proximal threaded nut 128 within the luer connector 102 (see, reference A). The proximal threaded nut 128 may be conical in shape to remain fixed against a pull force of the guidance wire 122 (described below), thus providing a form closure inside the luer connector 102. The proximal threaded nut 128 may also be attached to the luer connector 102 by, e.g., glue, threads, a pin, etc., such that it remains secure.

The torque is also transmitted to a second threaded portion 132 of the double-threaded guidance wire 112 that engages a distal threaded nut 130 within the balloon structure 106 (see, reference B). The distal threaded nut 130 may be used as a radiopaque marker inside the balloon structure 106. A marker 134 may be provided that is fixed to a portion of the inner catheter body 110 that extends within the balloon structure 106. The marker 134 may be a radiopaque marker viewed using plain film x-ray, fluoroscopic x-ray, MRI or CT scanning.

The threads of the nuts 128 and 130, and the guidance wire 112 can be designed both with a left-hand thread or both with a right-hand thread. The threads can also be designed in opposite direction (one left-hand thread and the other right-hand thread). The interaction of the double-threaded guidance wire 112, proximal threaded nut 128, distal threaded nut 130 and the balloon structure 106 is described below with reference to FIGS. 7-10.

Figure 4:
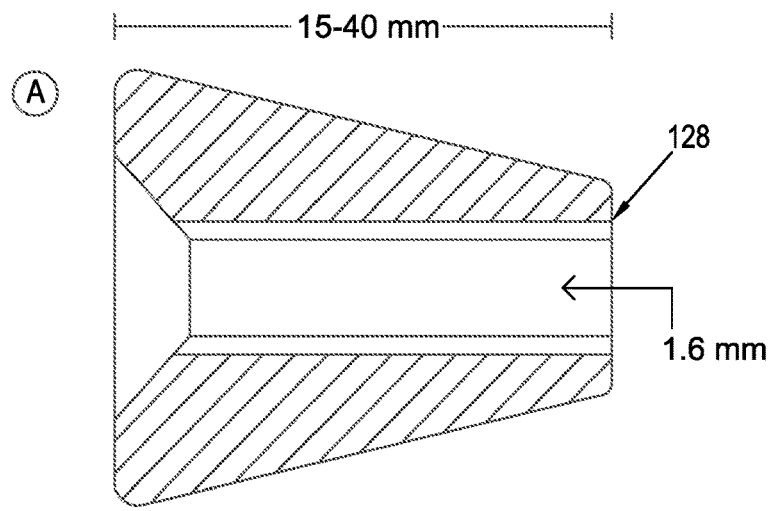
FIG. 4 is a cross-sectional view of a proximal threaded nut.
Figure 5:
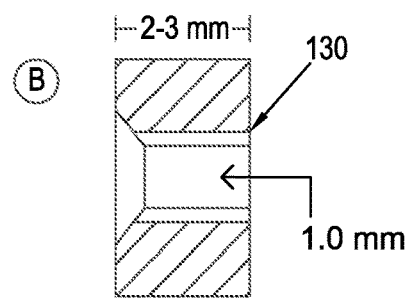
FIG. 5 is a cross-sectional view of a distal threaded nut.
Figure 6:
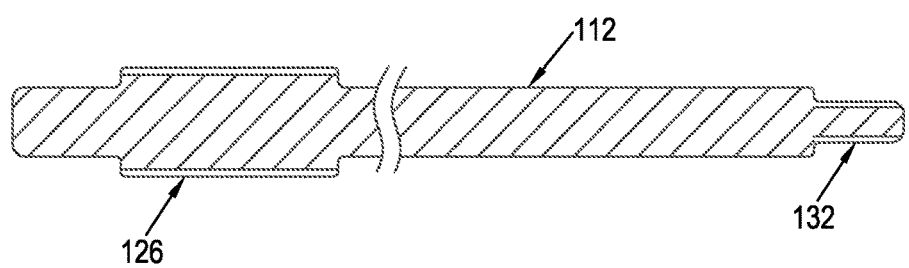
FIG. 6 is a cross-sectional view of the double-threaded guidance wire.

In some implementations, as shown in FIG. 4, the proximal threaded nut 128 may have a length of 15-40 mm. The diameter of the hole of the proximal threaded nut 128 may be approximately 1.6 mm. As shown in FIGS. 3 and 5, the distal threaded nut 130 may be inside the balloon structure 106 and have a length of 2-3 mm. The diameter of the hole of the distal threaded nut 130 may be approximately 1.0 mm.

The material from which the balloon structure 106 is made may possess various physical and mechanical properties to optimize its functional capabilities to compact cancellous bone. Such properties may include the ability to expand in volume, the ability to deform in a desired way when expanding and assume a desired shape inside bone, and/or the ability to withstand abrasion, tearing, and puncture when in contact with cancellous and/or cortical bone.

When compressing cancellous bone and/or creating a cavity, the expanded shape inside bone may be selected to optimize the formation of a cavity that, when filled with a selected material (e.g., PMMA, calcium phosphate, bone chips, etc.), provides support across the region of the bone being treated. In cases where the bone disease causing fracture is the loss of cancellous bone mass, as in osteoporosis, the selection of the shape of the balloon structure 106 inside bone may take into account the cancellous bone volume which should be compacted to achieve the desired therapeutic result. Another consideration for the selection of the shape of the balloon structure 106 is the amount that the targeted fractured bone region has been displaced or depressed. For example, the balloon structure 106 may have a predetermined length, such as 10 mm, 15 mm or 20 mm, selected based on the amount of displacement. The expansion of the balloon structure 106 inside a bone can elevate or push the fractured cortical wall back to or near its anatomic position occupied before fracture occurred.

Figure 7:
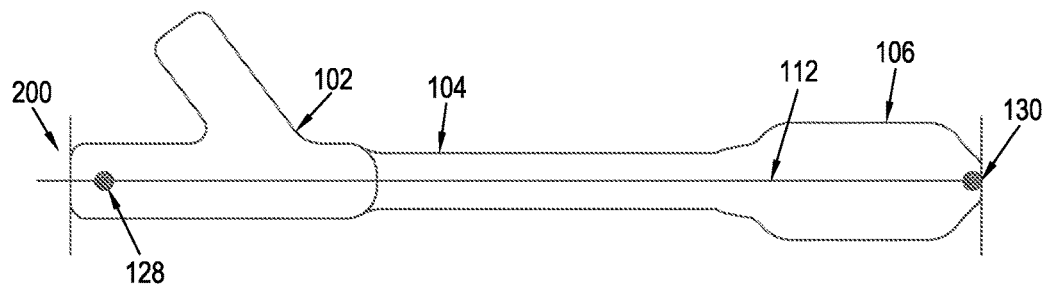
FIG. 7 illustrates an implementation to inflate the balloon structure with the double-threaded guidance wire attached thereto.
Figure 7:
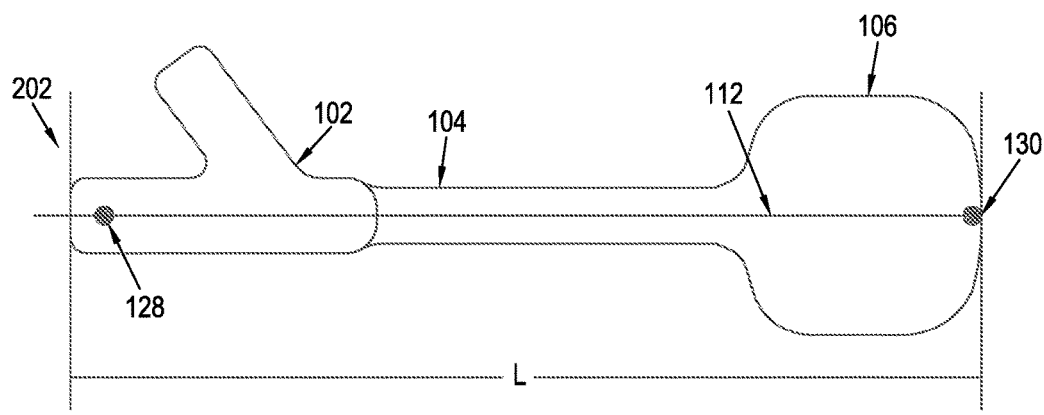
Figure 8:
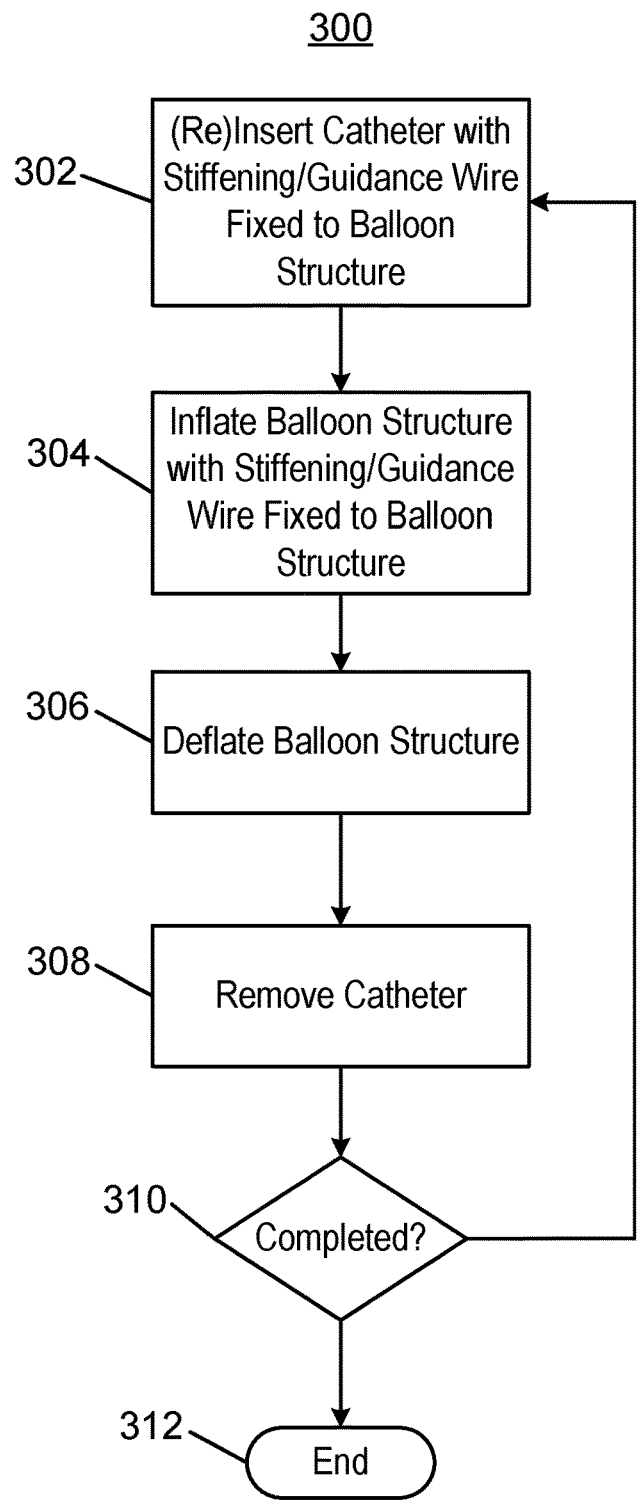
FIG. 8 is operational flow diagram of exemplary processes that are performed as part of a procedure using the implementation of FIG. 7.

Referring now to FIG. 7, there is illustrated an implementation of the tool 100 wherein the double-threaded guidance wire 112 remains fixed to the balloon structure 106 during inflation of the balloon structure 106. FIG. 8 illustrates an associated operational flow diagram 300 of exemplary processes that are performed as part of a procedure using the tool 100 in such an implementation. At 302, when the catheter tube assembly 104 of the tool 100 is delivered into a patient, the double-threaded guidance wire 112 is fixed to the distal threaded nut 130 of the balloon structure 106 (see, reference 200). In the delivered state, the balloon structure 106 may be folded such that the tool 100 has an axial length L.

At 304, the balloon structure 106 is then inflated with the double-threaded guidance wire 112 fixed to the distal threaded nut 130 (see, reference 202). The inflation of the balloon structure 106 may, e.g., compress or create a cavity within cancellous bone and/or elevate the cortical wall of the spine. As shown at 202, the tool 100 substantially remains at the axial length L in the inflated state.

At 306, the balloon structure 106 is then deflated and the catheter tube assembly 104 may be removed at 308. Because the double-threaded guidance wire 112 remains fixed to the balloon structure 106 through the threaded engagement of the second threaded portion 132 to the distal threaded nut 130, the balloon structure 106 remains substantially at its original axial length L.

At 310, if the procedure using the tool 100 is completed, then the process ends 312. However, if the procedure involves further balloon inflations, then at 310, the catheter tube assembly 104 may be reused and reinserted (at 302) and the balloon structure 106 reinflated for subsequent use. Thus, the tool 100 may be reused either in the same vertebral body or another vertebral body in the same patient because the balloon structure 106 remains supported by the double-threaded guidance wire 112 and, as such, has a known size.

Figure 9:
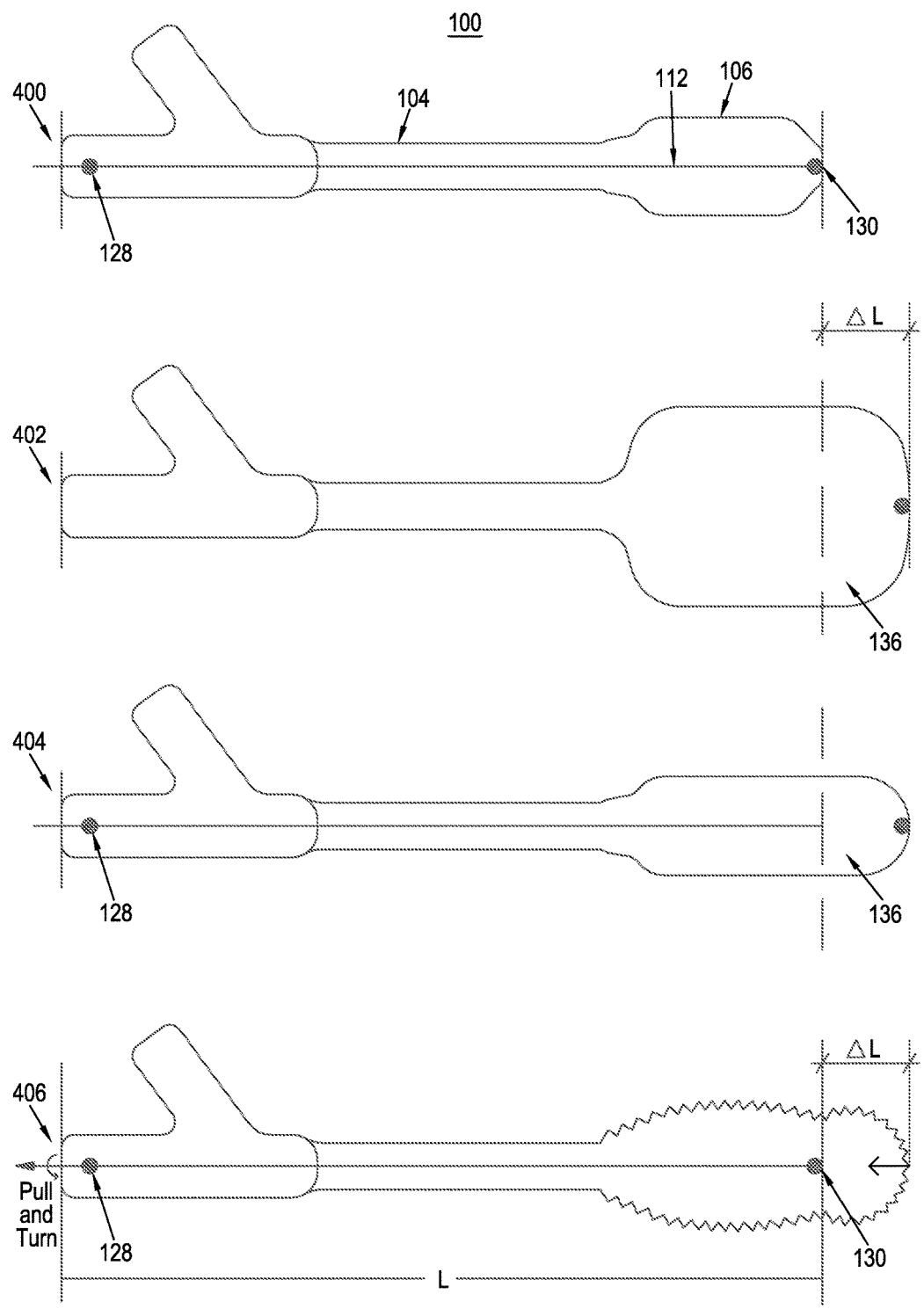
FIG. 9 illustrates an implementation to inflate the balloon structure where the double-threaded guidance wire is removed during inflation of the balloon structure and reinserted to withdraw the balloon structure.
Figure 10:
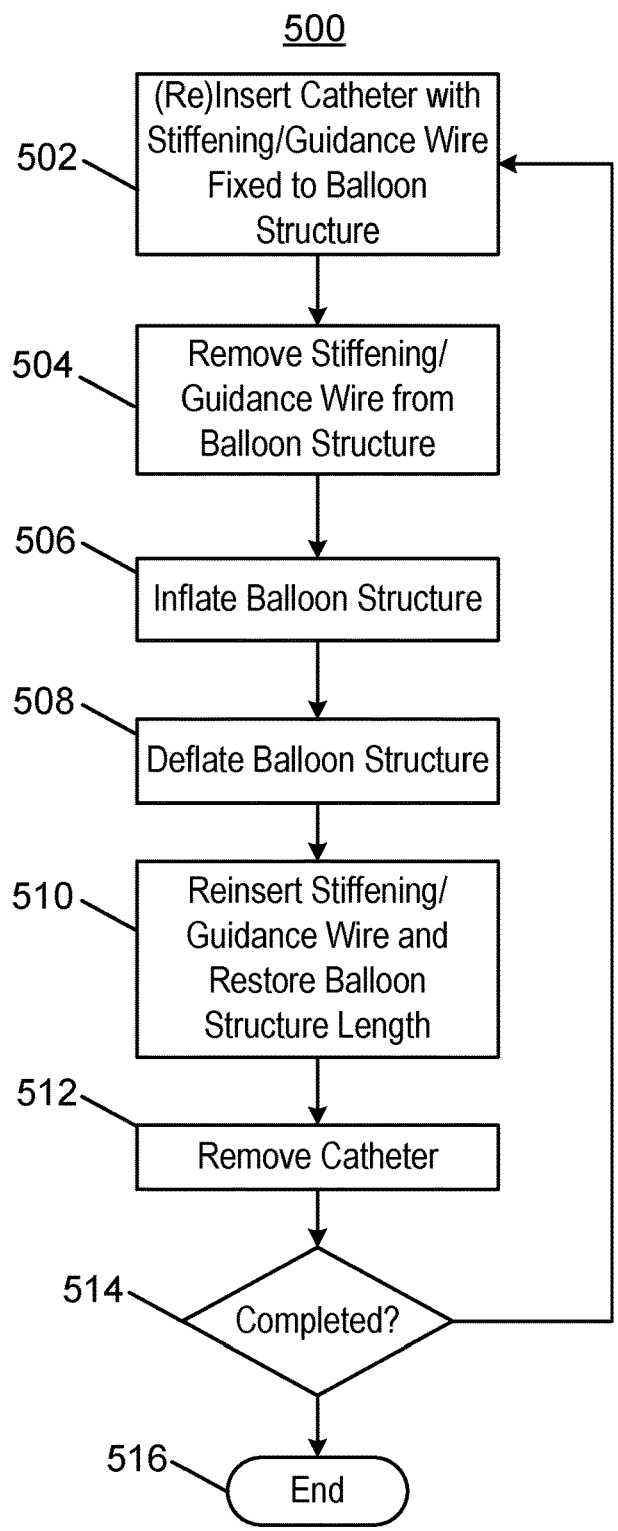
FIG. 10 operational flow diagram of exemplary processes that are performed as part of a procedure using the implementation of FIG. 9.

Referring now to FIG. 9, there is illustrated an implementation wherein the double-threaded guidance wire 112 is removed from the balloon structure 106 during inflation of the balloon structure 106. FIG. 10 is an associated operational flow diagram 500 of exemplary processes that are performed as part of a procedure using the tool 100 in such an implementation. At 502, when the catheter tube assembly 104 of the tool 100 is delivered into a patient, the double-threaded guidance wire 112 is fixed to the distal threaded nut 130 of the balloon structure 106 (see, reference 400). In the delivered state, the balloon structure 106 may be folded.

At 504, the double-threaded guidance wire 112 is removed, and the balloon structure 106 is then inflated at 506 (see, reference 402). The inflation of the balloon structure 106 compresses or creates a cavity within cancellous bone and/or elevates the cortical wall. The inflation of the expanding balloon structure 106 also expands the balloon structure 106 in the axial direction by an amount (designated by ΔL) to create an expansion area 136 that is unsupported.

At 508, the balloon structure 106 is then deflated and the double-threaded guidance wire 112 is reinserted into catheter tube assembly 104 at 510 (see, reference 404). For example, the double-threaded guidance wire 112 may be rotated such that the second threaded portion 132 engages the distal threaded nut 130 in the balloon structure 106. As shown in reference 406, the double-threaded guidance wire 112 is pulled back to engage the first threaded portion 126 within the proximal threaded nut 128. As such, the length of the balloon structure 106 is restored to the original starting position, as indicated by the arrows and dashed lines.

At 512, the catheter tube assembly 104 may be removed. At 514, if the procedure using the tool 100 is completed, then the process ends 516. However, if the procedure involves further balloon inflations, then at 514, the catheter tube assembly 104 may be reinserted (at 502) and the process repeats for the subsequent insertion(s). The tool 100 may be reused either in the same vertebral body or another vertebral body in the same patient.

In the implementations above, the interaction of the double-threaded guidance wire 112, proximal threaded nut 128 and distal threaded nut 130 locks the guidance wire 112 into a position such that the balloon structure 106 is returned to its original length after inflation. It is noted that any locking mechanism that returns the balloon structure 106 its original length after inflation may be used in the tool 100.

Although the distal threaded nut 130 has been described as being within the balloon structure 106, the distal threaded nut may be either inside or outside of the balloon structure 106. For example, the thread may be part of a rivet that is outside the balloon structure 106 and forms part of a tip of the balloon structure 106.

The subject matter described above is provided by way of illustration only and should not be construed as limiting.

Various modifications and changes may be made to the subject matter described herein without following the example embodiments and applications illustrated and described, and without departing from the true spirit and scope of the present invention, which is set forth in the following claims.

What is claimed is:

1. A reusable tool for use in a vertebral augmentation procedure, comprising:
   a catheter structure including an outer catheter member and an inner catheter member extending within the outer catheter member, where an interior diameter of the outer catheter member is larger than an exterior diameter of the inner catheter member to define an interior passage between the outer and inner catheter member;
   an expandable structure connected to the outer catheter member; and
   a guidance wire extending through an interior lumen of the inner catheter member and beyond a distal end of the inner catheter member, a distal end of the guide wire coupled to a distal end of the expandable structure; and
   a luer connector connected to the catheter structure, the connector having an inflation port in fluid communication with the passage defined between the inner and outer catheter members, where the passage is configured to convey a pressurized flowable medium into the expandable structure.

2. The tool of claim 1, wherein the inner catheter member extends through and beyond a distal end of the outer catheter member and into the expandable structure.

3. The tool of claim 1, wherein the luer connector is a Y-shaped luer connector,
   wherein the luer connector includes a proximal port at a proximal end of the luer connector, the inflation port extending from a side of the luer connector between the proximal port and a distal end of the luer connector.

4. The tool of claim 3, wherein the guidance wire includes a first threaded portion adapted to engage a proximal thread provided on an interior surface of the luer connector.

5. The tool of claim 4, wherein the luer connector includes a proximal luer fitting provided at the proximal port, and a luer cap rotatably coupled to the proximal luer fitting,
   wherein the guidance wire extends through the luer fitting and is coupled to the luer cap such that rotation of the luer cap results in a corresponding rotation of the guidance wire,
   wherein when the guidance wire is rotated by the luer cap is retracted from the catheter structure via engagement between the first threaded portion and the proximal thread.

6. The tool of claim 5, wherein the guidance wire includes a second threaded portion adapted to engage a distal thread provided at a distal end of the expandable structure.

7. The tool of claim 6, wherein the distal thread is provided on a threaded nut coupled to a distal tip portion of the balloon.

8. The tool of claim 6, wherein rotation of the luer cap 116 results in a corresponding rotation of the guidance wire to engage the distal thread.

9. The tool of claim 6, wherein a direction of the first threaded portion is opposite a direction of the threads of the second threaded portion, such that rotation of the guidance wire within the connector does not allow the guidance wire to disengage from the expandable structure,
   wherein an overall length of the expandable structure along an axial direction remains constant between an unexpanded and expanded state of the expandable structure.

10. The tool of claim 5, wherein the proximal thread is provided on a proximal threaded nut included in the luer connector, the proximal threaded nut coupled to the luer connector such that an axial location of the proximal threaded nut is fixed against a pull force of the guidance wire.

11. The tool of claim 10, wherein the proximal threaded nut is rotationally fixed within the luer connector.

12. The tool of claim 10, wherein the proximal threaded nut is conical in shape.

13. The tool of claim 3, wherein a proximal end of the inner catheter member and a proximal end of the outer catheter member are jointly coupled to the luer connector, the outer catheter member coupled to a luer fitting provided on the distal end of the luer connector,
   wherein the proximal end of the inner catheter member extends within the luer connector beyond the coupled proximal end of the outer catheter member.

14. The tool of claim 13, wherein the outer catheter member is coupled to the luer fitting provided on an interior surface of the luer connector.

15. The tool of claim 13, wherein the extended proximal end of the inner catheter member is coupled to the luer connector at a location external to the opening of the proximal port.

16. The tool of claim 1, wherein the guidance wire includes a first threaded portion adapted to engage a proximal thread provided on an interior surface of the luer connector,
   wherein the guidance wire includes a second threaded portion adapted to engage a distal thread provided at a distal end of the expandable structure,
   wherein a diameter of the first threaded portion is greater than a diameter of the second threaded portion.

17. The tool of claim 16, wherein the diameter of an intermediate portion of the guidance wire extending between the first threaded portion and the second threaded portion is less than the diameter of the first threaded portion and greater than the diameter of the second threaded portion.

18. A reusable tool for use in a vertebral augmentation procedure, comprising:
   a catheter structure including an outer catheter member and an inner catheter member extending within the outer catheter member, where an interior diameter of the outer catheter member is larger than an exterior diameter of the inner catheter member to define an interior passage between the outer and inner catheter member;
   an expandable structure connected to the outer catheter member; and
   a guidance wire extending through an interior lumen of the inner catheter member and beyond a distal end of the inner catheter member, a distal end of the guide wire coupled to a distal end of the expandable structure; and
   a luer connector connected to the catheter structure, the connector having an inflation port in fluid communication with the passage defined between the inner and outer catheter members, where the passage is configured to convey a pressurized flowable medium into the expandable structure,
   wherein a proximal end of the inner catheter member and a proximal end of the outer catheter member are jointly coupled to the luer connector, the proximal end of the inner catheter member is coupled to a distal end of the luer connector, the proximal end of the outer catheter member is coupled to a luer fitting located between the inflation port and the distal end of the luer connector.

19. The tool of claim 18, wherein the outer catheter member is coupled to the luer fitting provided on an outer surface of the luer connector, wherein an outer diameter of the luer fitting is less than an outer diameter of the luer connector proximate the inflation port.

20. The tool of claim 18, wherein the luer connector is a Y-shaped luer connector including a proximal port at a proximal end of the luer connector, the inflation port extending from a side of the luer connector between the proximal port and the distal end of the luer connector, wherein the luer connector includes a luer cap rotatably coupled to the luer connector at the proximal port, wherein the guidance wire extends through the proximal port and is coupled to the luer cap such that rotation of the luer cap results in a corresponding rotation of the guidance wire.

21. The tool of claim 20, wherein the guidance wire includes a first threaded portion adapted to engage a proximal thread provided on an interior surface of the luer connector, and a second threaded portion adapted to engage a distal thread provided at a distal end of the expandable structure, a diameter of the first threaded portion being greater than a diameter of the second threaded portion, wherein when the guidance wire is rotated by the luer cap is retracted from the catheter structure via engagement between the first threaded portion and the proximal thread.

\* \* \* \* \*